June 28, 1955 J. PARMENTIER Plant Pat. 1,400
ROSE PLANT
Filed Oct. 22, 1954
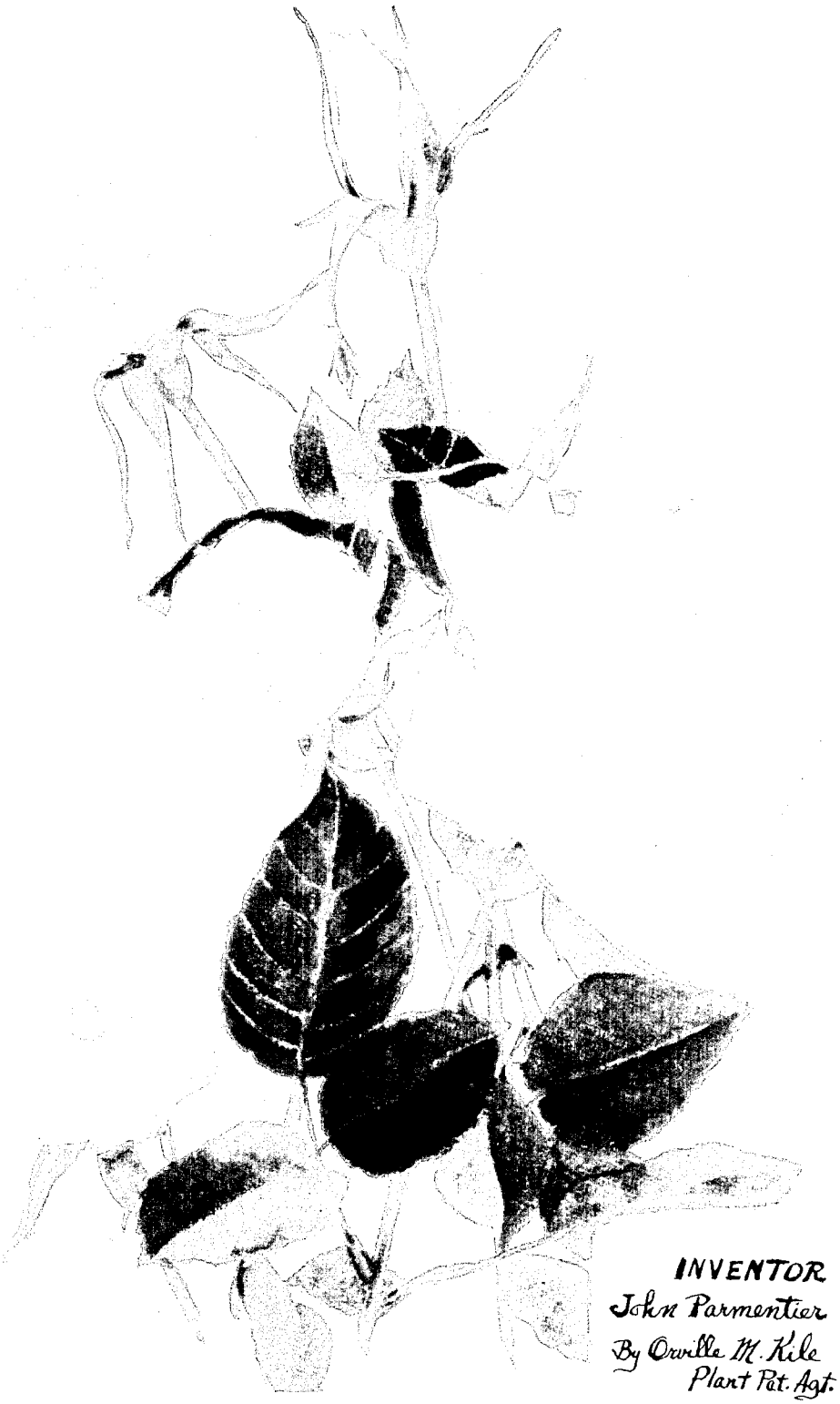
INVENTOR
John Parmentier
By Orville M. Kile
Plant Pat. Agt.

United States Patent Office

Plant Pat. 1,400
Patented June 28, 1955

1,400

ROSE PLANT

John Parmentier, Bayport, N. Y., assignor to Parmentier's Roses, Bayport, N. Y.

Application October 22, 1954, Serial No. 464,195

1 Claim. (Cl. 47—61)

My present invention pertains to a new and improved variety of hybrid tea rose plant and is the result of definite breeding efforts made by met at greenhouses in Bayport. It is the result of a cross between the varieties Queen Mary (Plant Pat. #249) and Katherine Pechtold (unpatented).

The outstanding novel features of my new variety are its brilliant flowers of unusual color, combined with strong growth and good production.

I have asexually reproduced my new variety at our greenhouses by means of budding, and its characteristics appear to be permanent.

The accompanying illustration shows in approximately true colors, a group of six specimens of the flower of my new variety in varying stages of opening, together with portions of the stems and foliage.

In the following detailed description, color plate numbers refer to Ridgway's Color Standards and Nomenclature. Other color names refer to the ordinary dictionary meaning of the term.

THE PLANT

Growth habit: Strong grower; branching and bushy. It combines the better growing characteristics of both parents, resulting in a bushy, healthy grower.

Blooming habit: Prolific producer of good flowers, exceeding the production of either parent. Makes an excellent greenhouse rose for cut flowers.

Foliage:

*Quantity.*—Plentiful but not over-abundant.

*Type.*—Pinnately compound, usually with 3 to 5 leaflets.

*Size.*—Medium. Terminal leaflet measures 2 to 2½ inches long by 1¼ to 1¾ inches wide.

*Color.*—Approximately Forest Green (Pl. XVII), frequently with red veins. Biscay Green (Pl. XVII) on under surface.

*Shape.*—Usually elliptical with rounded base and tip except for an acuminate apex. Serrations are fine and sharp.

*Texture.*—Substantial but not heavy or leathery.

*Rachis.*—Slender; smooth except for several very sharp thorns on under side; usually reddish tinged.

*Stipules.*—Long, narrow and clinging, with long points.

Stems: Stiff; strong; Oil Green (Pl. V), frequently red-tinged; covered with many thorns.

*Thorns.*—Plentiful, ranging from small at top of stem to very large on lower stem. Sharp; outward to downward-pointing; usually red-tinged with green points.

THE FLOWER

Bud:

*Color.*—There is no color in Ridgway's which is adequate to describe this bud, but it falls between Peach Red and Scarlet Red (both Plate I), with a large aiglet of Light Cadmium Yellow (Plate IV) fusing into the principal color. Over-all color might be called scarlet-copper.

*Size.*—Medium. Averages about 1½ inches long when beginning to spread.

*Shape.*—Pointed, opening in somewhat globular form.

Bloom:

*Size.*—Medium, averaging about 3½ inches in diameter.

*Form.*—High-centered, with outer petals reflexing early. Later, in most instances, the petals reflex and have a tendency to quill, the center usually remaining covered by the small petals which are folded and somewhat quilled.

*Color.*—When first open, outer petals are same color as bud, with inner petals considerably lighter tones of the same color—falling between Strawberry Pink and Peach Red (both Plate I)—and there is a larger amount of yellow showing at the base than on the outer surface. The color changes after the flower has fully opened, and after three or four days becomes approximately Deep Vinaceous (Pl. XXVII) at the tips on the inner surface of the petals, and Eugenia Red (Pl. XIII) on the outer surface. In its very last stages before the petals drop, the color becomes a deep apricot yellow with dull pink to mauve edge and bright yellow aiglet. Only at this stage is the inner surface of the central petals visible.

*Petalage.*—Averages about 65 petals.

*Longevity.*—Medium to good.

*Calyx.*—Large; bright green, approximately Cosse Green (Plate V).

*Sepals.*—Broad; reflex early; usually two or three of the five are foliaceous.

Petals:

*Substance.*—Petals are substantial but not heavy and leathery.

*Shape.*—Somewhat obcordate; cupped in early stages of opening, but often quilled and reflexed in later stages.

*Fragrance.*—Slight.

*Behavior.*—Drop off cleanly.

Reproductive organs:

*Pistils.*—A great many; closely bunched. Styles—exposed portion is dark red. Medium in length and slightly uneven. Stigmas—small and deep greenish yellow.

*Stamens.*—Fewer than the pistils and surrounding them. Filaments—uneven lengths; curved, cupping around bunched pistils. Bright yellow, approximately Light Cadmium Yellow (Pl. IV). Anthers—medium size; dark yellow.

Having thus disclosed my invention, I claim:

The new and distinct variety of hybrid tea rose plant, substantially as herein shown and described, combining the principal good qualities of both parents and characterized particularly by the unusual scarlet-copper coloring of its flowers; the light green foliage; its strong bushy growth; and its prolific production of flowers.

No references cited.